United States Patent [19]

Metz et al.

[11] 4,156,003
[45] May 22, 1979

[54] TREATMENT OF HYPERTENSION WITH COMBINATION OF CLOFIBRINIC ACID OR CLOFIBRATE WITH CINNARIZINE

[75] Inventors: Gunter Metz, Blaubeuren; Manfred Specker, Blaubeuren-Weiler, both of Fed. Rep. of Germany

[73] Assignee: Ludwig Merckle K.G., Chem. Pharm. Fabrik, Fed. Rep. of Germany

[21] Appl. No.: 936,513

[22] Filed: Aug. 24, 1978

[51] Int. Cl.² ............... A61K 31/495; A61K 31/235; A61K 31/19
[52] U.S. Cl. .................... 424/250; 424/308; 424/317
[58] Field of Search ................ 424/250, 308, 317

[56] References Cited

U.S. PATENT DOCUMENTS 2,882,271  4/1959  Janssen ................... 542/440

FOREIGN PATENT DOCUMENTS 2502678  7/1976  Fed. Rep. of Germany ........... 424/250

OTHER PUBLICATIONS

Schmitt, Med. Welt, vol. 25, 1974, pp. 1096–1099.
Hauss, Chem. Abs. vol. 84, 1976.
Schmitt, Chem. Abs. vol. 83, 1975.
Van Nueten, Chem. Abs., vol. 76, 1972.

*Primary Examiner*—Anna P. Fagelson
*Attorney, Agent, or Firm*—Roylance, Abrams, Berdo & Farley

[57] ABSTRACT

The use of the combination of clofibrinic acid or clofibrate with cinnarizine for the treatment of hypertension in humans is disclosed.

9 Claims, No Drawings

TREATMENT OF HYPERTENSION WITH COMBINATION OF CLOFIBRINIC ACID OR CLOFIBRATE WITH CINNARIZINE

This invention relates to a new use for a known pharmaceutical combination. More specifically, this invention relates to the use of a combination of clofibrinic acid or related compound with cinnarizine for the treatment of hypertension.

2-(p-Chlorophenoxy)-2-methylpropionic acid (clofibrinic acid) having the formula

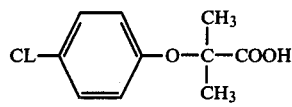

and its ethyl ester (clofibrate) are well known therapeutic compounds for the treatment of hyperlipemia and are contained in several commercially available drugs. These compounds are not known to have hypotensive activity.

1-Cinnamyl-4-diphenylmethylpiperazine (cinnarizine) having the formula

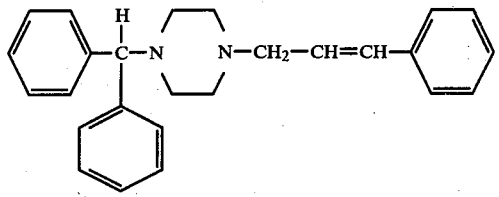

disclosed in U.S. Pat. No. 2,882,271, is known to have antihistaminic and cerebral and peripheral vasodilatory effects. It is reported in the literature (Arzneim.-Forsch, *Drug Research*, 21, 1541, 1971 and Medizinische Welt, 21, 2132, 1970) that cinnarizine when administered in a therapeutic single dose up to 75 mg. offers no hypotensive action, even in hypertensive patients. Further, it is reported in Medizinische Welt, 25, 1096, 1974, that in a test using hypertensive rats, cinnarizine did not influence the hypertensive condition in any way.

German Patent Specification No. OS 25 02 678, published July 29, 1976, discloses that the combination of cinnarizine and clofibrinic acid or related compounds is useful in the treatment of hyperlipemia and that this combination has a good anti-thrombotic effect and in particular a peripheral vasodilatory effect.

It has now been discovered that the combination of ingredients disclosed in German Patent Specification No. OS 25 02 678 is useful in the treatment of hypertension. Thus, in accordance with the practice of this invention, there is administered to a host animal, including man, which is afflicted with hypertension, a drug comprising a combination of cinnarizine and clofibrinic acid or related compound selected from the group consisting of compounds having the formula

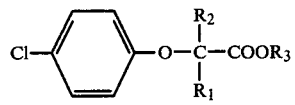

wherein $R_1$ and $R_2$ may each be a hydrogen atom or a lower alkyl group of from 1 to 4 carbon atoms and $R_3$ is a hydrogen atom, a lower alkyl group of from 1 to 4 carbon atoms or a pharmaceutically acceptable metal atom having a valence of from 1 to 3. The combination is administered in an amount sufficient to lower the blood pressure of said host. By "hypertension" is meant systolic hypertension and/or diastolic hypertension.

As used herein, the term "lower alkyl group" is intended to include methyl, ethyl, propyl and isopropyl groups. The term "pharmaceutically acceptable metal atom" is intended to include sodium, potassium, calcium, magnesium and aluminum atoms.

In accordance with this invention, the drug comprising the combination previously described may be administered in any physiologically acceptable method, e.g., orally or parenterally. The ratio of clofibrinic acid or related compound to cinnarizine in the combination may be 2.5:1 up to 10:1, and is preferably, within the range of 5:1 to 8:1. The drug may be administered, preferably orally, in the form of e.g., soft or hard gelatin capsules, in doses of from 400 to 3000 mg./day, and, preferably, 500-2000 mg./day. The most preferred total dosage per day is 1000-1500 mg./day. The drug may be administered in single doses of 200-700 mg./unit and, preferably, 350-500 mg./unit. The suggested daily dosage for oral administration is 1-4 and preferably 2-3 soft gelatin capsules containing 425 mg. of clofibrate and 75 mg. of cinnarizine each. Similarly, hard gelatin capsules containing 300 mg. of clofibrinic acid and 50 mg. of cinnarizine per capsule may be used.

The following examples serve to illustrate the practice of this invention. In these examples, blood pressure was determined in accordance with WHO guidelines and is expressed in mm Hg. The limits of hypertension are equal to or greater than 160 for systolic and equal to or greater than 95 for diastolic. "S.d." refers to standard deviation.

EXAMPLE 1

Soft gelatin capsules containing 425 mg. of clofibrate and 75 mg. of cinnarizine per capsule were administered at the rate of two capsules per day over a four week period to a group of 40 patients. The total group of patients, primarily suffering from atherosclerotic or related diseases, contained 23 patients with systolic and/or diastolic hypertensions and 13 patients with normal blood pressure. The mean value of blood pressure for the group of 23 hypertensive patients was as follows:

systolic:
    before treatment: 179.6±18 s.d.
    after treatment: 134.8±15.8 s.d.
    % change: 24.9
diastolic:
    before treatment: 104.0±10.8 s.d.
    after treatment: 87.6±12.4 s.d.
    % change: 15.8

The mean value of blood pressure for the group of 17 patients having normal blood pressure was as follows:
systolic:
    before treatment: 142.1±8.5 s.d.
    after treatment: 141.5±16.1 s.d.
    no significant change:
diastolic:
    before treatment: 85.8±4.2 s.d.
    after treatment: 85.0±9.3 s.d.
    no significant change These results show that the combination of clofibrate and cinnarizine has a marked significant anti-hypertensive action while normal blood pressure is not influenced. These findings are surprising since conventional anti-hypertensive drugs such as reserpine or combinations of reserpine with other drugs generally affect patients with normal blood pressure as well as hypertensive patients.

EXAMPLE 2

A group of 10 hypotensive patients was treated for 20 days by administering two capsules daily. Each capsule contained 425 mg. of clofibrate and 75 mg. of cinnarizine. The mean value of the blood pressure for this group of patients was as follows:
systolic:
    before treatment: 109.6±10.5 s.d.
    after treatment: 102.5±11.9 s.d.
diastolic:
    before treatment: 68.5±4.2 s.d.
    after treatment: 62.5±9.0 s.d.

The results of this example show that the combination of clofibrate and cinnarizine has little or no effect on patients having lower than normal blood pressure.

EXAMPLE 3

Gelatin capsules each containing 425 mg. of clofibrate and 75 mg. of cinnarizine were administered to two groups of hypertensive patients. The first group was administered two capsules daily and the second group was administered three capsules daily. It was found that the hypotensive effect of the drug was very rapid within the first two days of treatment in a dosage of three times daily and was less rapid in a daily dosage of two capsules. The dose depending difference in hypotensive action is lost within one to four weeks of treatment, resulting in approximately equal normalization of mean blood pressure values following one to four weeks of treatment. In the group of patients which were treated with two capsules daily, the mean value of systolic blood pressure before treatment was 171.7±11.3 s.d., following one day of treatment was 161.9±14.2 s.d., and following 20 days of treatment was 129.6±20.6 s.d.; and the diastolic blood pressure before treatment was 99.6±8.6 s.d.; following one day of treatment was 92.4±17.1 s.d., and following 20 days of treatment was 75.0±9.3 s.d. For the group of patients receiving three capsules daily, the mean value of systolic blood pressure was 176.0±10.7 s.d. before treatment, 149.2±26.5 s.d. following one day of treatment, and 123.6±16.3 s.d. following 20 days of treatment; while the diastolic blood pressure was 100.0±11.5 s.d. at the beginning of treatment, 89.1±15.9 s.d. after one day of treatment, and 83.2±12.7 s.d. after 20 days of treatment.

We claim:

1. A process for the treatment of a host animal which is afflicted with hypertension which comprises administering to said animal in an amount sufficient to lower the blood pressure of said host animal, a drug comprising a combination of cinnarizine and clofibrinic acid or related compounds selected from the group consisting of compounds having the formula:

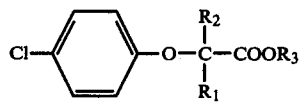

wherein $R_1$ and $R_2$ may each be a hydrogen atom or a lower alkyl group of from 1 to 4 carbon atoms and $R_3$ is a hydrogen atom, a lower alkyl group of from 1 to 4 carbon atoms or a pharmaceutically acceptable metal atom having a valence of from 1 to 3 wherein the ratio of clofibrate or related compounds to cinnarizine in the combination is 2.5:1 to 10:1.

2. A process as defined in claim 1 wherein said host animal is a human being.

3. A process as defined in claim 2 wherein the ratio of clofibrate or related compounds to cinnarizine in the combination is 5:1 to 8:1.

4. A process as defined in claim 2 wherein said drug is administered in the form of a soft or hard gelatin capsule.

5. A process as defined in claim 2 wherein said drug is administered in a dose of from 400–3000 mg./day.

6. A process as defined in claim 2 wherein said drug is administered in a dose of from 500–2000 mg./day.

7. A process as defined in claim 2 wherein said drug is administered in a dose of from 1000–1500 mg./day.

8. A process as defined in claim 2 wherein said drug is administered in a single dose of from 200–700 mg./unit.

9. A process as defined in claim 2 wherein said drug is administered in a single dose of from 350–500 mg./unit.

* * * * *